United States Patent [19]

Mikhail

[11] Patent Number: 5,718,707
[45] Date of Patent: Feb. 17, 1998

[54] METHOD AND APPARATUS FOR POSITIONING AND COMPACTING BONE GRAFT

[76] Inventor: W. E. Michael Mikhail, 4203 Shamley Green, Toledo, Ohio 43623

[21] Appl. No.: 787,140

[22] Filed: Jan. 22, 1997

[51] Int. Cl.[6] ................................................ A61B 17/56
[52] U.S. Cl. .................................................. 606/94; 606/93
[58] Field of Search ................................... 606/94, 95, 93, 606/92, 86; 604/181, 187

[56] References Cited

U.S. PATENT DOCUMENTS

| | | | |
|---|---|---|---|
| 4,274,408 | 6/1981 | Nimrod | 604/165 |
| 4,337,773 | 7/1982 | Raftopoulos et al. | 606/62 |
| 4,338,925 | 7/1982 | Miller | 606/94 |
| 4,341,206 | 7/1982 | Perrett et al. | |
| 4,399,814 | 8/1983 | Pratt, Jr. et al. | |
| 4,623,353 | 11/1986 | Buechel et al. | 623/23 |
| 4,678,471 | 7/1987 | Noble et al. | 623/16 |
| 4,686,972 | 8/1987 | Kurland | |
| 4,706,659 | 11/1987 | Matthews et al. | |
| 4,751,922 | 6/1988 | DiPietropolo | |
| 4,815,454 | 3/1989 | Dozier, Jr. | |
| 4,846,161 | 7/1989 | Roger | |
| 4,860,735 | 8/1989 | Davey et al. | |
| 4,865,608 | 9/1989 | Brooker, Jr. | 623/23 |
| 4,873,969 | 10/1989 | Huebsch | |
| 4,881,536 | 11/1989 | Noble et al. | 606/94 |
| 4,896,662 | 1/1990 | Noble | 606/94 |
| 4,919,153 | 4/1990 | Chin | 606/93 |
| 4,919,673 | 4/1990 | Willert et al. | 623/23 |
| 4,919,679 | 4/1990 | Averill et al. | 623/23 |
| 4,963,155 | 10/1990 | Lazzeri et al. | 623/23 |
| 4,986,826 | 1/1991 | Roger | 606/82 |
| 4,994,065 | 2/1991 | Gibbs et al. | 606/92 |
| 4,994,085 | 2/1991 | Sawai et al. | 623/23 |
| 5,015,817 | 5/1991 | Kranz | 623/22 |
| 5,021,063 | 6/1991 | Tager | 623/23 |
| 5,047,035 | 9/1991 | Mikhail et al. | 606/93 |
| 5,047,061 | 9/1991 | Brown | 623/23 |
| 5,061,287 | 10/1991 | Feiler | 623/16 |
| 5,078,746 | 1/1992 | Garner | 623/16 |
| 5,085,548 | 2/1992 | Moyles | |
| 5,108,405 | 4/1992 | Mikhail et al. | 606/96 |
| 5,116,377 | 5/1992 | Skriptitz et al. | 623/23 |
| 5,192,282 | 3/1993 | Draenert | 606/65 |
| 5,192,283 | 3/1993 | Ling et al. | 606/93 |
| 5,197,841 | 3/1993 | Tanaka | |
| 5,201,769 | 4/1993 | Schutzer | 623/23 |
| 5,314,489 | 5/1994 | Hoffman et al. | 623/22 |
| 5,366,441 | 11/1994 | Crawford et al. | 604/53 |
| 5,443,469 | 8/1995 | Smith | 606/86 |
| 5,470,336 | 11/1995 | Ling et al. | 606/105 |
| 5,480,452 | 1/1996 | Hofmann et al. | 623/23 |
| 5,507,830 | 4/1996 | DeMane et al. | 623/32 |
| 5,514,135 | 5/1996 | Earle | 606/93 |

FOREIGN PATENT DOCUMENTS

| | | |
|---|---|---|
| 2615097 | 5/1987 | France. |
| 0 315 283 | 11/1988 | United Kingdom. |
| 92/03993 | 3/1992 | WIPO. |

OTHER PUBLICATIONS

Kenneth J. Hock, M.D., "Economy is the Mother of a Cement Removal Technique", *Orthopedics Today*, pp. 18–19.
John N. Insall, M.D., et al., "Principles and Techniques of Knee Replacement", published in 1983 by New York Society for the Relief of the Ruptured and Crippled, pp. 20–21.
John Insall, M.D. and Albert H. Burstein, Ph.D., "Insall/Burstein™ Total Knee System" Pamphlet.
W.E. Michael Mikhail, M.D. and Lars Weidenhielm, M.D., "The CPT Hip Prosthesis" Pamphlet (1994).
Osteonics Restoration Cemented Hip System For Revision Surgery, 4 pages.
Waldes Truarc Retaining Rings, Jan. 1981, p. 5 (Selector Guide).

*Primary Examiner*—Guy V. Tucker
*Attorney, Agent, or Firm*—Emch, Schaffer, Schaub & Porcello, Co., L.P.A.

[57] ABSTRACT

A method and apparatus for introducing and compacting bone graft material in an enlarged femoral cavity including a dispenser having a barrel containing bone graft material and a cannulated ejector positionable over a guide wire for both ejecting bone graft material from the barrel and compacting the bone graft material while being guided on the guide wire.

10 Claims, 7 Drawing Sheets

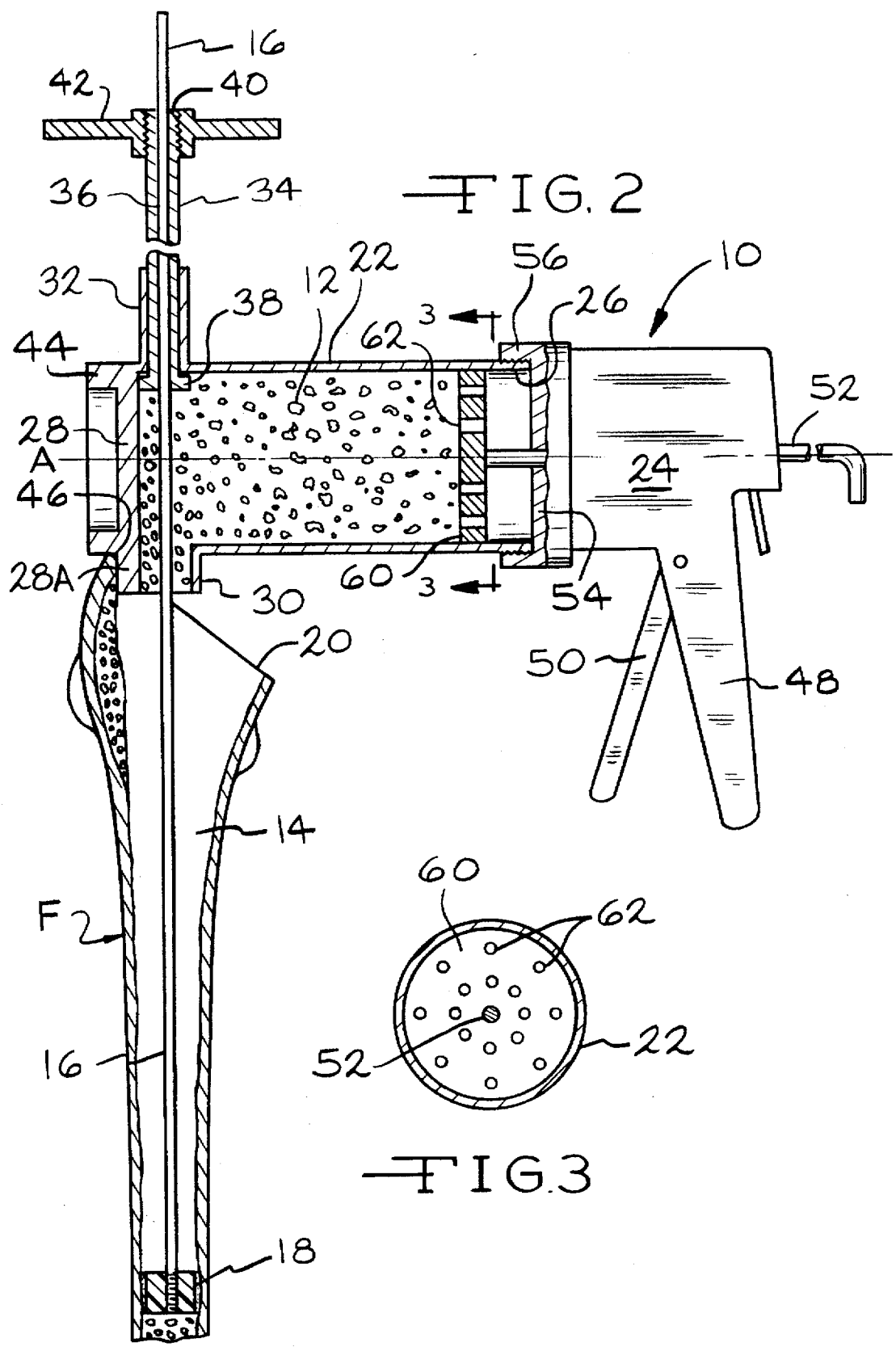

5,718,707

1

METHOD AND APPARATUS FOR POSITIONING AND COMPACTING BONE GRAFT

BACKGROUND OF THE INVENTION

In performing hip prosthesis surgery, it is frequently necessary or desirable to place bone graft material in the intramedullary canal of the femur in order to promote new bone growth. This is particularly true in revision surgery in which a previously implanted femoral prosthesis is removed and replaced with a new prosthesis. The reason for this is that the cavity formed by removal of the previously implanted prosthesis and any old bone cement, particulate debris, membrane, beads and other remnants associated with cemented or cementless femoral prosthesis removal results in a cavity significantly larger than is desired for implantation of a new prosthesis.

In U.S. Pat. Nos. 5,047,035 and 5,108,405, of which I am a co-inventor, a method and apparatus for reaming a cavity in a femur are disclosed. In U.S. Pat. Nos. 5,192,283 and 5,470,336, of which I am also a co-inventor, there is disclosed method and apparatus for compacting bone graft material using a cannulated tamp.

Under the present application there is provided a method and apparatus for both dispensing bone graft material directly into a femoral cavity and for at least preliminarily compacting bone graft material in such cavity while utilizing a guide wire to ensure proper positioning.

IN THE DRAWINGS

FIG. 2 is a elevational view partly in section showing the dispenser ready for dispensing bone graft material into a femoral cavity.

FIG. 3 is a sectional view taken along line 3—3 of FIG. 2.

BEST MODE OF CARRYING OUT INVENTION

Figure 1:
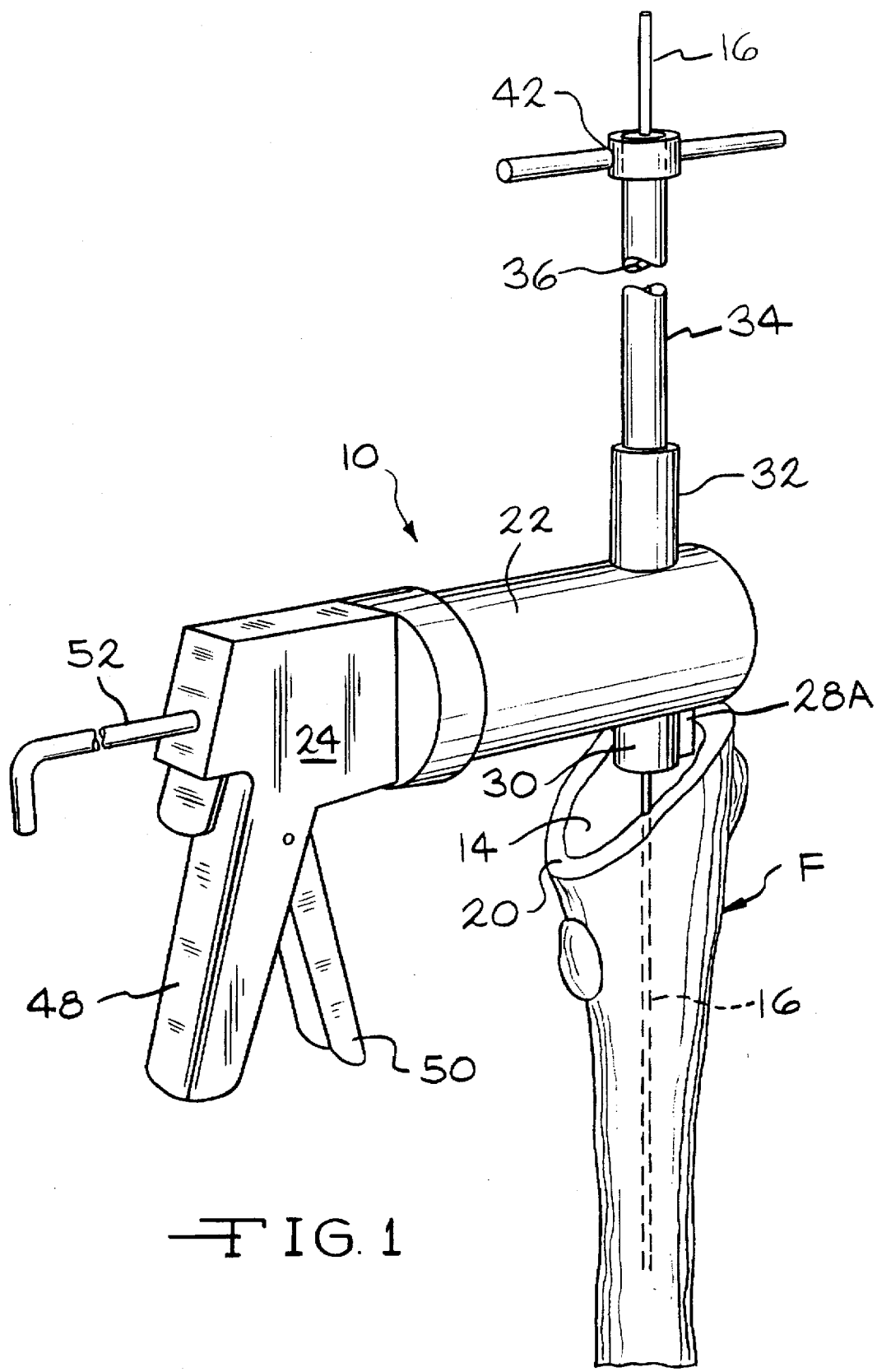
FIG. 1 is a perspective view showing one embodiment of the dispenser of the present invention aligned with the proximal end of a cut femur having an enlarged cavity into which bone graft material is to be dispensed.

Referring now to FIGS. 1 through 3, there is shown a dispenser 10 for introducing bone graft material 12 into a cavity 14 of a femur F. The cavity 14 as shown in FIGS. 1 and 2 is significantly larger than the prosthesis intended to be implanted therein. Such enlarged cavity may result from the fact that the patient previously had another femoral prosthesis implanted in the femur F which failed or was otherwise required to be removed. In removing the previously implanted prosthesis in revision surgery, it is necessary to remove not only the failed prosthesis but also any bone cement utilized therewith or debris of a cementless prosthesis. The cavity 14 may be prepared according to the teachings of my prior U.S. Pat. Nos. 5,047,035 and 5,108,405 in which a reamer is utilized in combination with a guide wire in order to ensure proper alignment of the cavity 14.

As shown in FIG. 2, a guide wire 16 is threadedly engaged to a plug or cement restrictor 18 positioned in the distal end of the cavity. The guide wire extends out of the proximal end 20 of the cavity 14 to a position extending beyond such proximal end a distance sufficiently far for the dispenser 10 to be positioned thereover, a distance, for example, of 15 to 25 cm.

The dispenser 10 as shown in FIGS. 1 and 2, includes a barrel 22 and an actuator 24 secured thereto, for example by threaded engagement.

The barrel 22 includes a cylindrical wall extending from a receiving end 26, to which the actuator 24 is removably engaged, to an end wall 28. Extending downwardly (as viewed in FIGS. 1 and 2) at substantially right angles to the axis A of the cylindrical wall of the barrel 22 is a dispensing nozzle 30. As can be seen in FIG. 2, the dispensing nozzle 30 is adjacent end wall 28 and an extension 28A of such end wall 28 forms a portion of the dispensing nozzle 30. Extending upwardly (as viewed in FIGS. 1 and 2), in alignment with the dispensing nozzle 30, is a tubular section 32.

Figure 4:
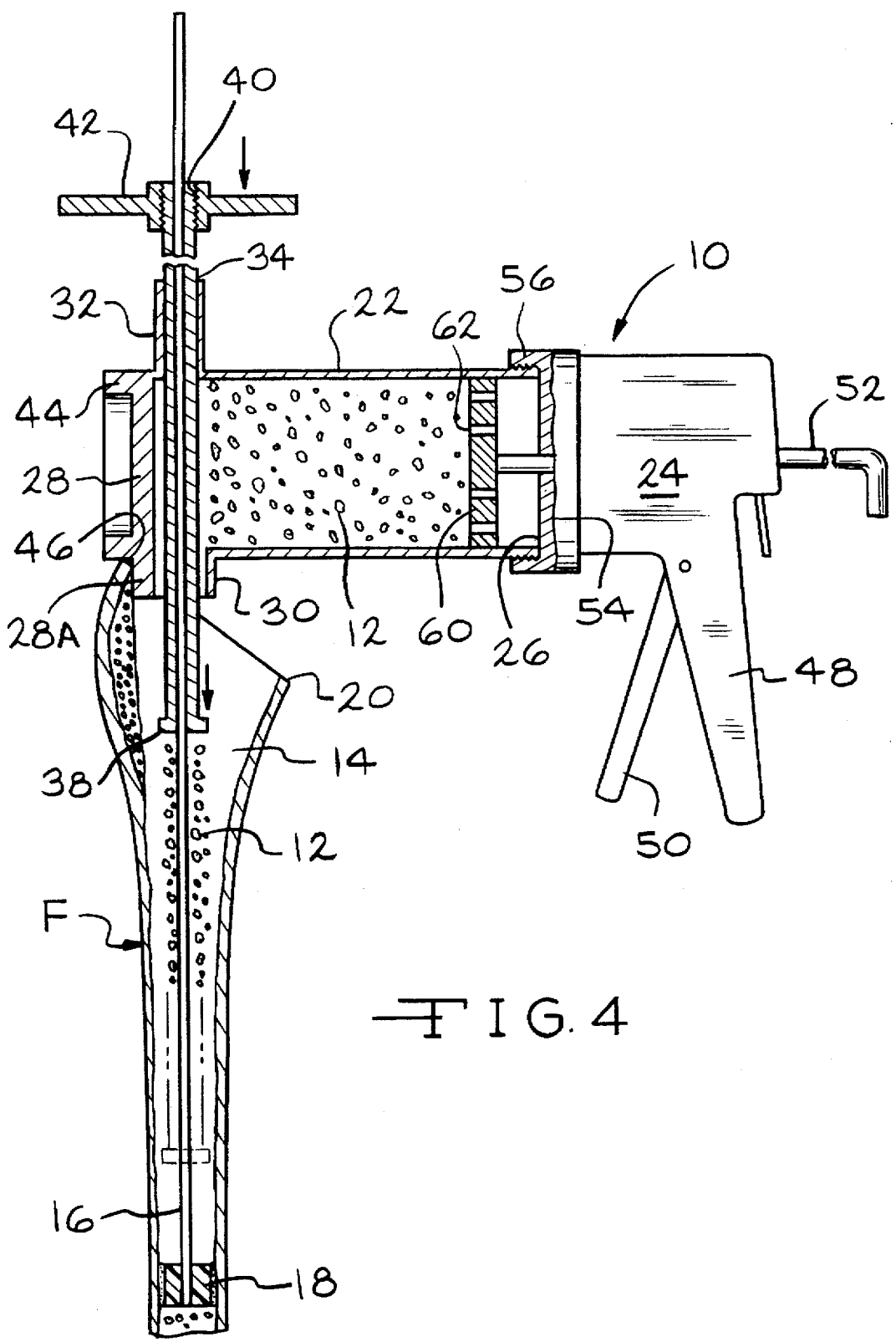
FIG. 4 is a view similar to FIG. 2 showing ejection of bone graft material from the dispenser and into the cavity and showing in dashed lines extension of the plunger to a position for compacting.

Mounted in sliding engagement with the interior surface of the tubular section 32 is a cannulated ejector member 34 having a central passageway 36 sized to receive the guide wire 16 and to slideably move relative to such guide wire 16. The ejector member 34 has an enlarged head 38 which is sized smaller than the interior wall of tubular section 32 to prevent withdrawal of the head 38 through such tubular section 32 thereby preventing disassociation of the ejector member 34 from the barrel 22. The enlarged head 38 is slightly smaller than the interior surface of the dispensing nozzle 30 so that it may readily slide therethrough as shown by comparing FIG. 3 with FIG. 4. The tubular section 32 extends upwardly to a threaded end portion 40 to which may be engaged a T-bar 42 having a threaded collar engaged to the threaded end 40. The T-bar 42 may be used for manually sliding the ejector member 34 from the raised or retracted position shown in FIG. 2 to the lowered or extended position shown in FIG. 4. If desired, the T-bar could be an integral pat of the ejector member.

Extending along the axis A from the end wall 28 is a short cylindrical section 44, the lower portion of which cooperates with end wall extension 28A to define a corner support 46 which may rest upon the proximal end 20 of the prepared femur, preferably along the lateral side to stabilize the dispenser 10.

The actuator 24 includes a handle 48 and a pivotally mounted trigger 50 attached to a rachet-type push bar 52 such as those commonly used with caulking guns. The push bar 52 extends through the end wall 54 of a collar member 56 which is threadedly engaged or locked to the receiving end 26 of the barrel 22. Supported on the end of the push bar 52 is a plunger 60 sized to be slidably engaged with the interior surface of the barrel 22. The plunger 60 has a plurality of apertures 62 formed therein for permitting the escape of any liquid material such as marrow, fat and blood which may have accumulated in the bone graft 12.

In operation, bone graft 12 is inserted in the barrel 22 and the actuator 24 is threadedly engaged to the barrel 22 with the plunger 60 in the retracted position shown in FIG. 2. Preferably, the ejector member 34 will be in its raised position upon the introduction of bone graft 12 into the barrel 22 and engagement of the actuator 24 thereto. The dispenser 10 thus loaded is positioned over the guide wire 16, with the guide wire 16 extending through the passageway 36 of the ejector member. Preferably, the dispenser 10 is supported at the proximal end 20 of the femur F with the corner support 46 engaging such proximal end 20 at the lateral cortex. With the dispenser 10 thus positioned, the ejector member 34 is pushed downwardly by manual gripping of the T-bar 42 so that the enlarged head 38 pushes bone graft material out of the dispensing nozzle 30 and into the cavity 14. Preferably, the ejector member 34 has sufficient length such that the head 38 can compact the bone graft 12 substantially completely to the restrictor 18 as shown in phantom lines in FIG. 4.

Figure 5:
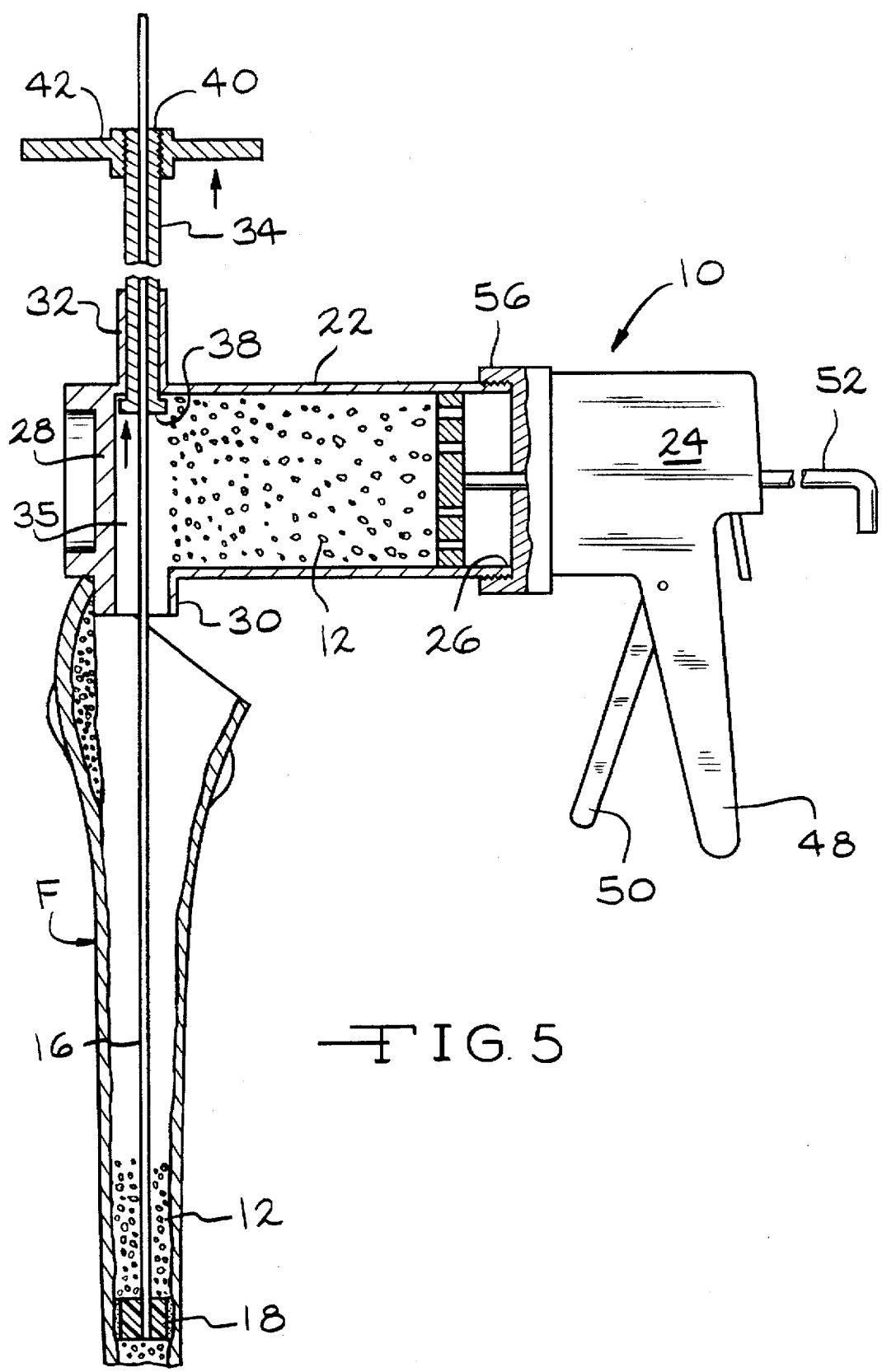
FIG. 5 is a view showing retraction of the ejector member preparatory to dispensing another quantity of bone graft material into the cavity.
Figure 6:
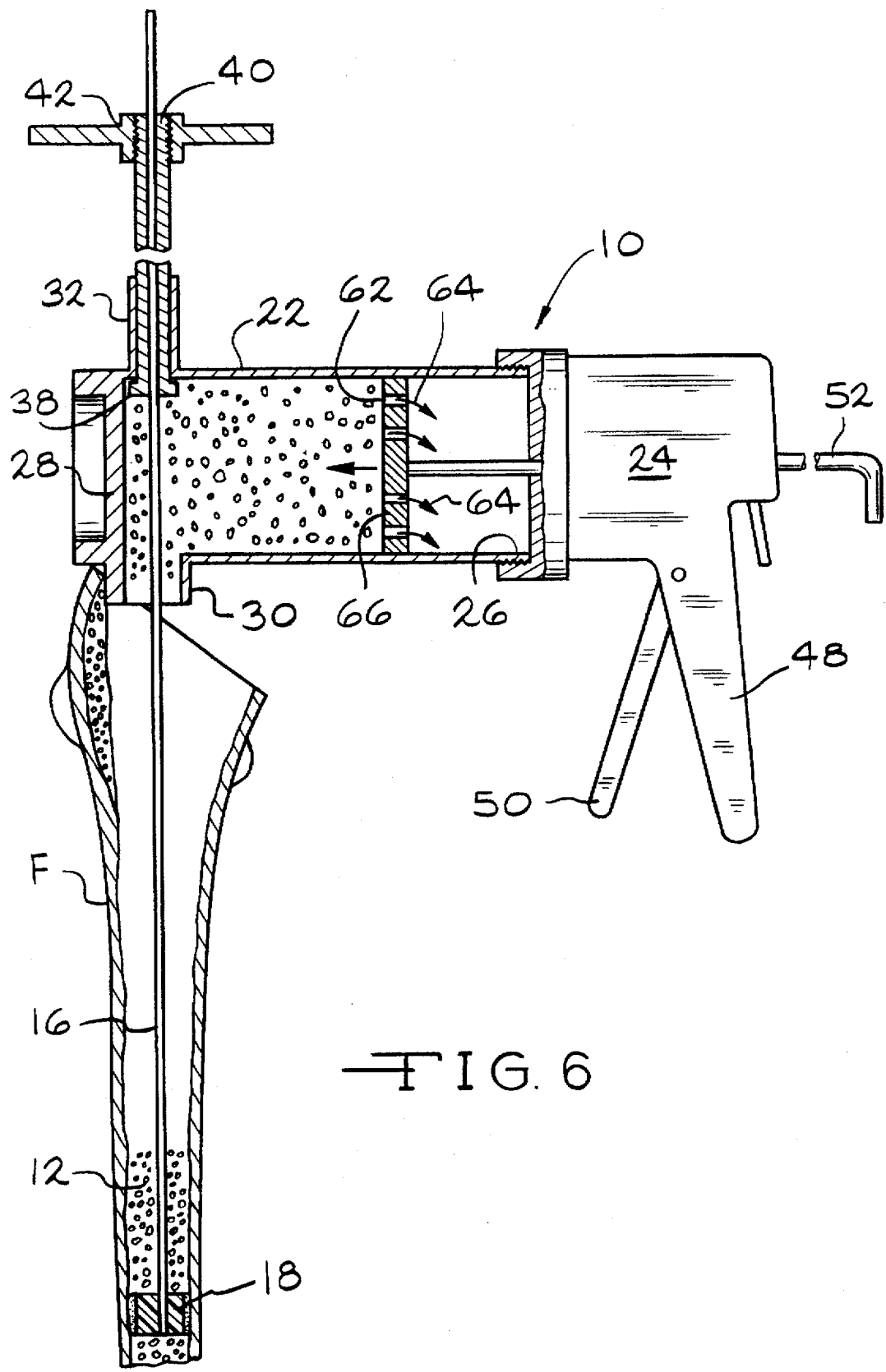
FIG. 6 is a view similar to FIG. 5 showing movement of the plunger to push the bone graft material into alignment with the dispensing ejector member.

The ejector member 34 is then raised to the position shown in FIG. 5 leaving a space 35 from which the bone graft 12 was ejected. The trigger 50 is then actuated to force the plunger 60 further into the barrel 22 causing bone graft 12 to fill the space 35 with the portion adjacent the wall 28 being aligned with the dispensing nozzle 30 and the enlarged head 38 ready for ejection upon lowering of the ejector member 34. As shown in FIG. 6, as the plunger moves toward the end wall 28 to move bone graft material 12 into position for ejection by the ejector member 34 and compressing such bone graft, undesirable liquids shown by arrows 64 in FIG. 6, may seep through the apertures 62.

Figure 7:
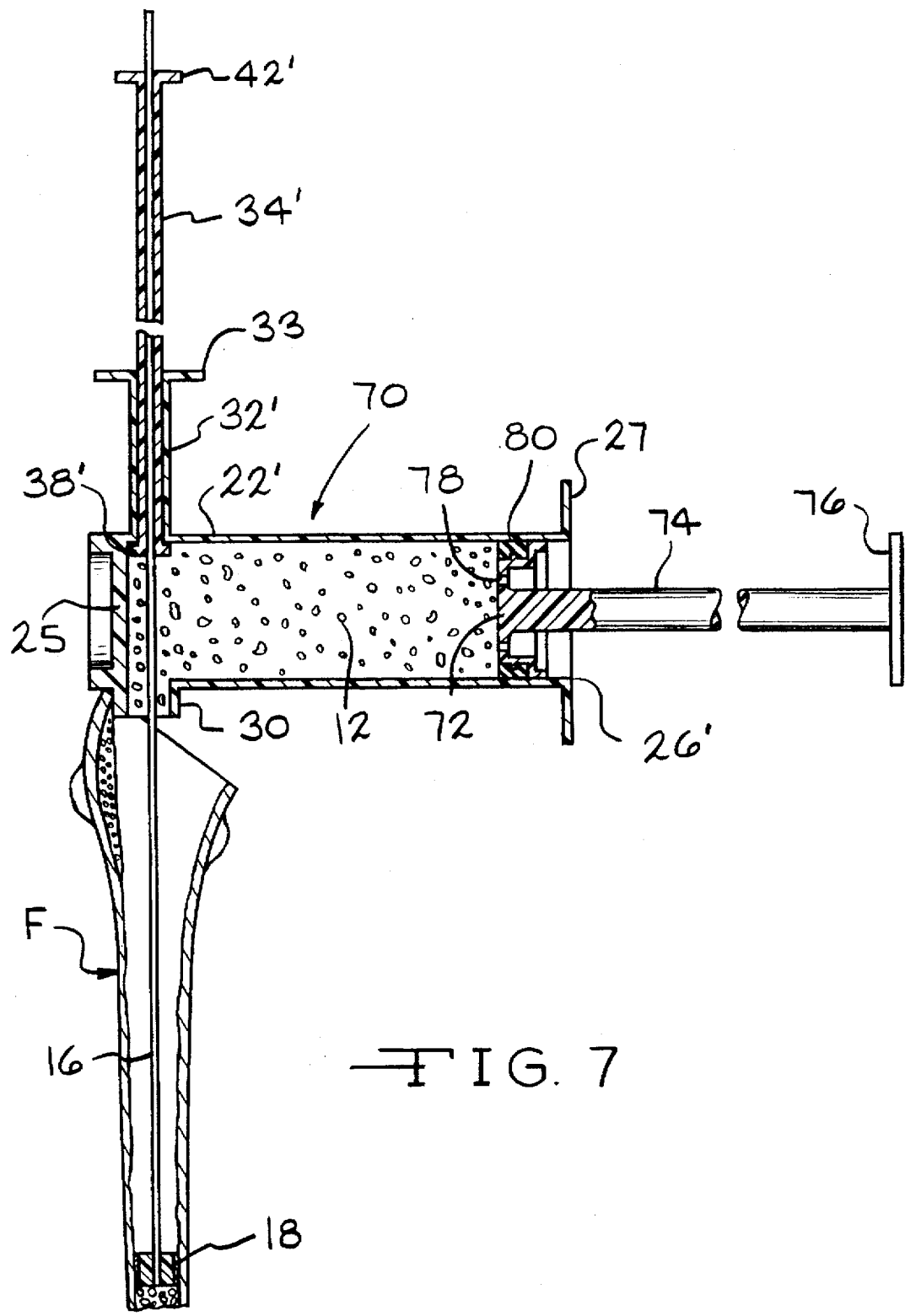
FIG. 7 is an elevational sectional view of a modified dispenser.

Referring now to FIG. 7, there is shown a modified dispenser 70 which is similar to the dispenser 10 except that, in place of having an actuator 24 threadedly engaged to the barrel 22, there is provided a plunger 72 which is moveable manually by a push bar 74 having an enlarged head 76. The plunger 72, push bar 74 and enlarged head 76 may be a desired medical grade plastic material and molded as a single, unitary article. As with the previous embodiment, the plunger 72 has a plurality of apertures 78 through which undesirable liquid material may be expelled from the bone graft material as the push bar 74 pushes the plunger 72 toward the end wall 28. The plunger 72 includes an annular groove in which is positioned an O-ring 80 which is slidingly and sealingly engaged to the interior wall of the barrel 22'. If desired, the barrel 22' may be provided with a radial flange 27 at its receiving end 26' to provide rigidity necessary to maintain the receiving end with a constant cross sectional configuration to snugly receive the plunger 72. The barrel 22' and all elements integral therewith (i.e. flange 27, end wall 28, dispensing nozzle 30, tubular section 32' with its flange 33) may also be formed of a suitable plastic such as polyethylene.

The ejector member 34' and integral T-bar 42' and enlarged head 38' may also be formed of plastic. When formed of plastic material, the dispenser 70 is sufficiently economical to be disposed of after a single use.

Figures 8, 9:
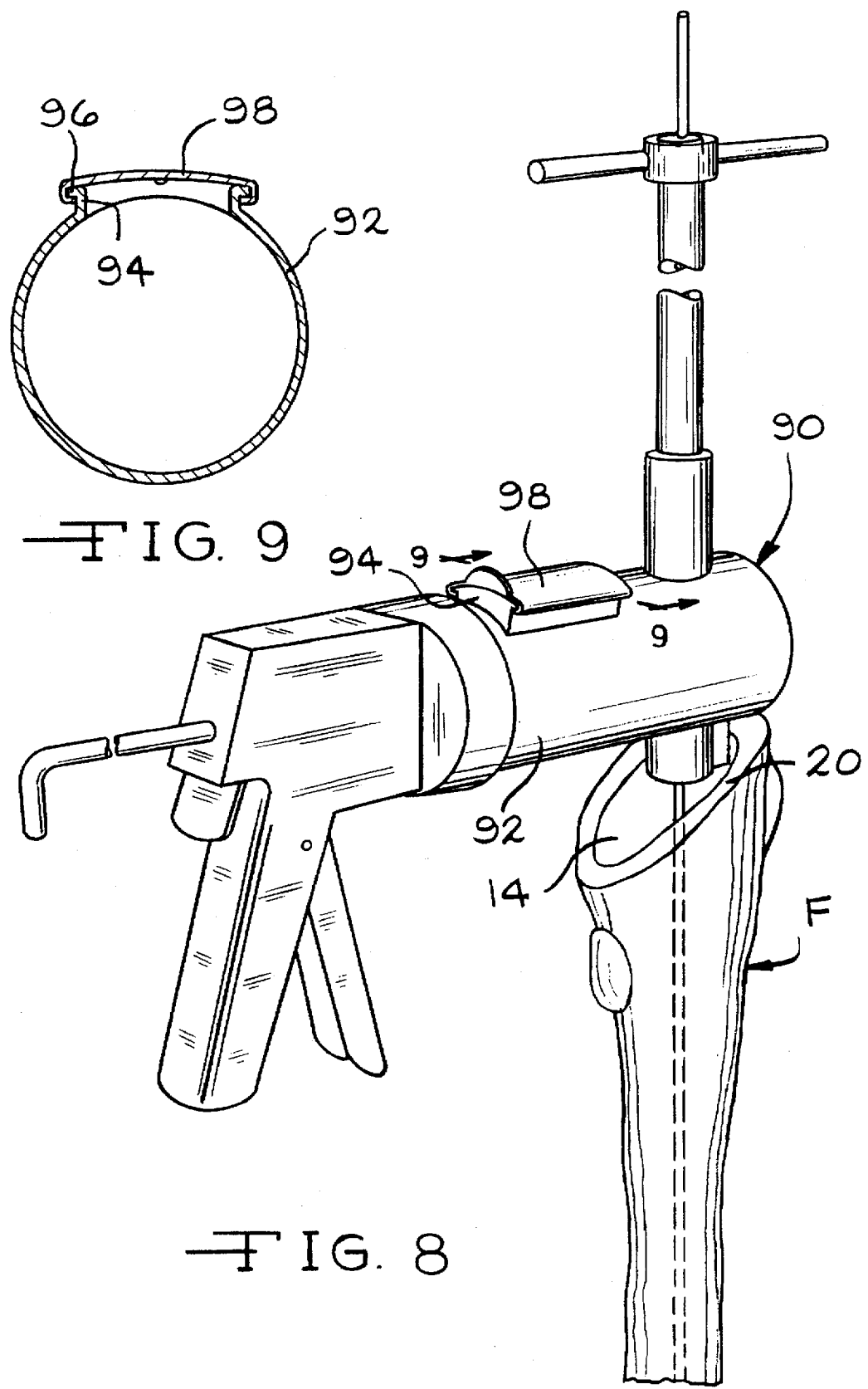
FIG. 8 is perspective view showing a further modified dispenser.
FIG. 9 is a sectional taken through 9—9 of FIG. 8.

Referring now FIGS. 8 and 9, there is shown a dispenser 90 which is similar to the dispenser 10 of the embodiment of FIGS. 1 through 6 with the exception that it is provided with access means to the interior of the barrel 92. As can be seen in FIGS. 8 and 9, the barrel has a rectangular wall 94 extending upwardly therefrom. A pair of parallel outwardly extending flanges 96 extend from two of the walls 94. Slideably engaged to the flanges 96 is a cover 98 which may be easily opened to introduce bone graft material into the barrel 92 without the necessity of removing the actuator 24.

Many modifications will become readily apparent to those skilled in art. Accordingly, the scope of the claims appended hereto should be determined only by the scope of the claims appended hereto.

I claim:

1. A method for preparing a cavity in a long bone for receiving a prosthesis having an elongated stem comprising:
   (a) forming an enlarged cavity extending from a distal end to a proximal end of said long bone;
   (b) positioning a guide wire in said enlarged cavity, said guide wire extending from said distal end and out of said proximal end;
   (c) positioning a dispenser containing bone graft material on said guide wire, said dispenser including an outlet and an elongated ejector member extending to an ejection end and having a passageway extending therethrough, said guide wire extending through said passageway and said outlet; and
   (d) moving said ejector member on said guide wire toward said outlet and said distal end to eject bone graft material through said outlet and into said enlarged cavity.

2. The method according to claim 1, further including extending said ejector member distally into said enlarged cavity to a position at which said ejection end compacts said ejected bone graft material.

3. The method according to claim 1, further including retracting said ejector member to move said ejection end through said outlet, positioning additional bone graft material between said ejection end and said outlet and moving said ejector member toward said distal end to cause said ejection end to expel additional bone graft material through said outlet and into said enlarged cavity.

4. The method according to claim 3, further including extending said ejector member distally into said enlarged cavity to a position at which said ejection end compacts said ejected bone graft material.

5. Apparatus for dispensing bone graft material into an enlarged cavity of a long bone comprising:
   (a) a body extending along a first axis and having a chamber for containing bone graft material, said body having an annular wall encircling said first axis and an outlet in said annular wall;
   (b) a plunger positioned in said body for movement said first axis, said plunger having an enlarged head moveable from a position axially spaced from said outlet to a position closer to said outlet;
   (c) an ejector member extending along a second axis and having an ejection end and a passageway extending therethrough for receiving a guide wire, said ejector member being movable from a position at which said ejection end is positioned within said body to a position extending through said outlet to eject bone graft material therefrom; and
   (d) a guide wire positioned in said passageway.

6. The apparatus for dispensing bone graft material according to claim 5, wherein said plunger enlarged head has an aperture through which liquid may flow.

7. The apparatus for dispensing bone graft material according to claim 5, wherein said annular wall is provided with a closeable opening for receiving bone graft material.

8. Apparatus for dispensing bone graft material into an enlarged cavity of a long bone comprising:
   (a) a body extending along a first axis and having a chamber for containing bone graft material, said body having an annular wall encircling said first axis and an outlet in said annular wall;
   (b) a plunger positioned in said body for movement along said first axis, said plunger having an enlarged head moveable from a position axially spaced from said outlet to a position closer to said outlet; and (c) an ejector member extending along a second axis and having an ejection end, said ejector member being movable from a position at which said ejection end is positioned within said body to a position extending through said outlet to eject bone graft material therefrom.

9. The apparatus for dispensing bone graft material according to claim 8, wherein said plunger enlarged head has an aperture through which liquid may flow.

10. The apparatus for dispensing bone graft material according to claim 8, wherein said annular wall is provided with a closeable opening for receiving bone graft material.

* * * * *

UNITED STATES PATENT AND TRADEMARK OFFICE
CERTIFICATE OF CORRECTION

PATENT NO.   : 5,718,707
DATED        : February 17, 1998
INVENTOR(S)  : W.E. Michael Mikhail It is certified that error appears in the above-identified patent and that said Letters Patent is hereby corrected as shown below:

In column 4, line 42, after "movement", please insert --along--.

Signed and Sealed this

Ninth Day of March, 1999

Attest:

Attesting Officer

Q. TODD DICKINSON

Acting Commissioner of Patents and Trademarks